(12) United States Patent
Mueller et al.

(10) Patent No.: US 7,810,929 B2
(45) Date of Patent: Oct. 12, 2010

(54) OPTICAL SYSTEM FOR A FUNDUS CAMERA

(75) Inventors: Lothar Mueller, Ottendorf (DE); Marco Hanft, Jena (DE); Uwe Lippmann, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 12/396,705

(22) Filed: Mar. 3, 2009

(65) Prior Publication Data

US 2009/0168018 A1  Jul. 2, 2009

Related U.S. Application Data

(63) Continuation of application No. 10/552,756, filed as application No. PCT/EP2004/002893 on Mar. 19, 2004, now Pat. No. 7,500,753.

(30) Foreign Application Priority Data

Apr. 10, 2003  (DE) ................ 103 16 416

(51) Int. Cl.
*A61B 3/10* (2006.01)
(52) U.S. Cl. ...................... 351/221; 351/205
(58) Field of Classification Search .......... 351/221, 351/205, 206
See application file for complete search history.

(56) References Cited

U.S. PATENT DOCUMENTS

| 2,586,973 | A | * | 2/1952 | McMillin | 351/206 |
| 2,978,956 | A | * | 4/1961 | Howell | 359/356 |
| 3,985,422 | A | * | 10/1976 | Mecklenborg et al. | 359/433 |
| 4,415,239 | A | | 11/1983 | Humphrey | |
| 4,730,910 | A | * | 3/1988 | Humphrey | 359/601 |
| 4,838,680 | A | | 6/1989 | Nunokawa | |
| 5,430,509 | A | * | 7/1995 | Kobayashi | 351/221 |
| 5,640,275 | A | | 6/1997 | Bourguignat et al. | |
| 7,500,753 | B2 | * | 3/2009 | Mueller et al. | 351/221 |

FOREIGN PATENT DOCUMENTS

DE  35 19 442  12/1985

* cited by examiner

*Primary Examiner*—Joseph Martinez
*Assistant Examiner*—James R Greece
(74) *Attorney, Agent, or Firm*—Frommer Lawrence & Haug LLP

(57) ABSTRACT

The invention is directed to an optical system for a fundus camera in which lens pairs are tilted relative to the imaging beam path to prevent flare. This tilting is carried out in two planes and these planes are preferably oriented perpendicular to one another.

6 Claims, 2 Drawing Sheets

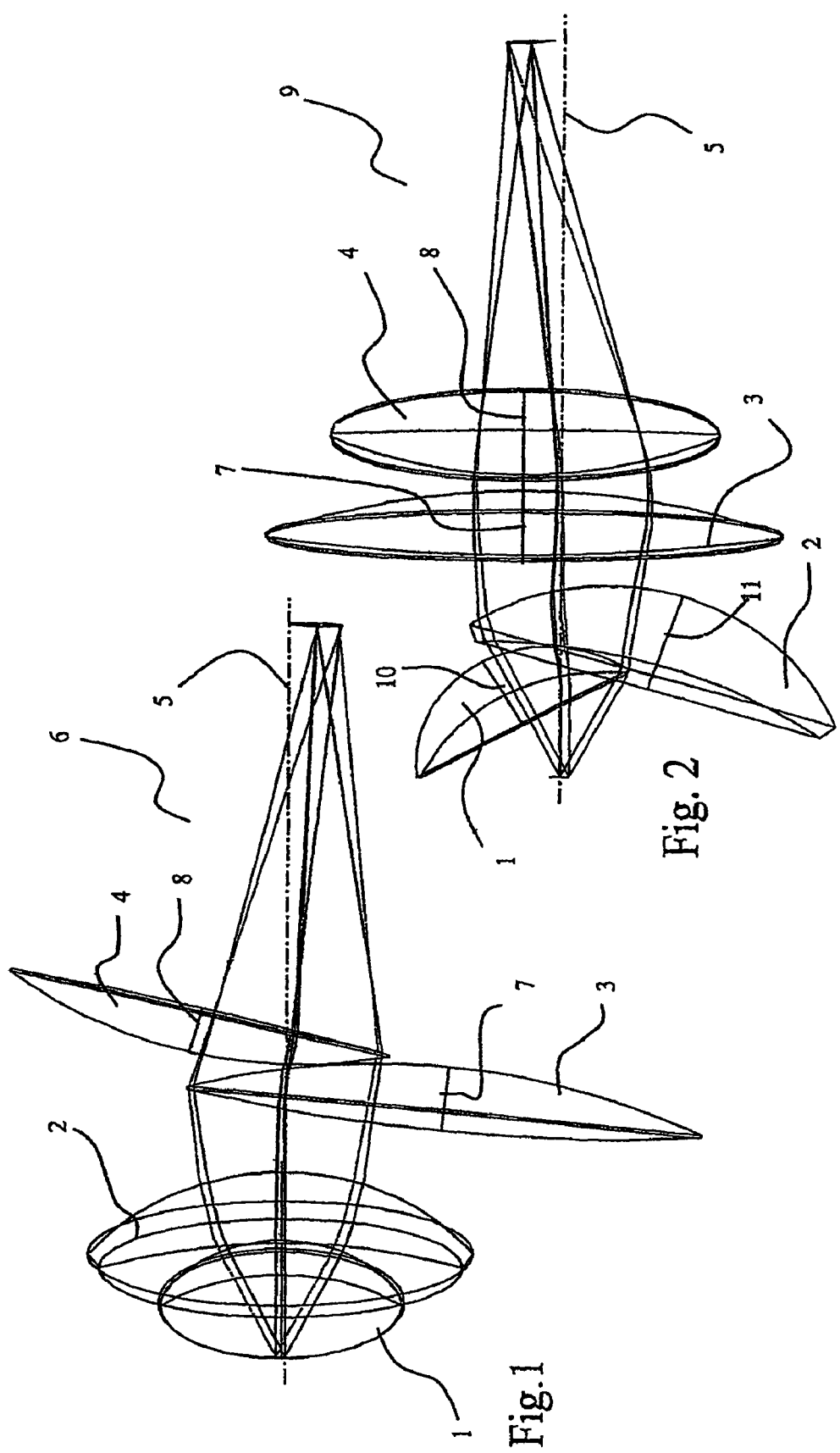

OPTICAL SYSTEM FOR A FUNDUS CAMERA

CROSS-REFERENCE TO RELATED APPLICATIONS

This is a continuation application of application Ser. No. 10/552,756 filed Jun. 20, 2006 now U.S. Pat. No. 7,500,753, which claims priority of International Application No. PCT/EP2004/002893, filed Mar. 19, 2004, and German Application No. 103 16 416.2, filed Apr. 10, 2003, the complete disclosures of which are hereby incorporated by reference.

BACKGROUND OF THE INVENTION a) Field of the Invention

The invention is directed to an optical system for a fundus camera which serves to image the ocular fundus. When imaging the ocular fundus with a camera of this type, flare generally results at the cornea and at surfaces of the optical system and has a degrading effect on the image quality.

In its basic construction, a fundus camera comprises a multiple-stage optical system. An opthalmoscope lens generates an intermediate image that is imaged by a sequential system (principal objective) on a film or a CCD matrix. The opthalmoscope lens is also a component part of the illumination.

b) Description of the Related Art

A particular problem in observing and photographing the fundus is posed by flare at the cornea and at the surfaces of the opthalmoscope lens because the light which is reflected by the retina and which carries the relevant image information is substantially less intense than the light that is reflected before entering the eye. Troublesome corneal flare is normally prevented by dividing the pupil of the eye. For this purpose, the opthalmoscope lens images an illumination ring in the pupil of the eye. The illumination rays reflected at the cornea miss the observation aperture. Only the area within the illumination ring is used for observation.

There are substantially two known concepts for suppressing flare at the opthalmoscope lens.

DE-OS 35 19 442 describes an optical system in which components of light that could enter the observation aperture by reflection at the opthalmoscope lens or cornea are masked out by "black-dot plates" which are arranged at a suitable location in the beam path and which are coated in a defined manner with light-absorbing layers. This method of suppressing reflections has come to be known as "anti-flare dot objective".

The proximity of the anti-flare dot to the field diaphragm is a disadvantage in this design. The absorption of individual light components can become visible as an inhomogeneous illumination of the ocular fundus. Ring-shaped shadows occur which degrade the image and accordingly impede evaluation by the ophthalmologist.

Another solution is described in U.S. Pat. No. 4,730,910. This solution does away with masking of determined light components within the illumination optics. Instead of the opthalmoscope lens, a multiple-lens objective is used whose lenses are tilted relative to one another in such a way that the direct flares at the glass-air interfaces do not enter the observation aperture. For this purpose, the optical axes of the lenses lie in a plane together with the optical axis of the observation beam path. This solution requires a considerable expenditure on mechanical mounting and has considerable problems with correcting imaging errors.

A system of the type mentioned above exhibits a clear difference between imaging scales in the meridional and sagittal section. Anamorphotic effects can be observed in object imaging as well as in pupil imaging (illumination). The images are distorted and there is no similarity of imaging. Further, the system exhibits coma and astigmatism when imaging the axial point and the imaging errors in the field are not symmetric with respect to rotation.

OBJECT AND SUMMARY OF THE INVENTION

It is the primary object of the invention to overcome the disadvantages of the prior art and to provide an optical system for a fundus camera which effectively eliminates flare at the optical surfaces from the imaging beam path and ensures extensive imaging fidelity.

This object is met by an optical system preferably for a fundus camera, which has a substantially coaxial illumination beam path and imaging beam path, and comprises a lens system of at least four lenses. At least two lenses are tilted with respect to their optical axes relative to the illumination beam path and imaging beam path. The optical axes of the lenses and the optical axis of the illumination beam path and imaging beam path lie in a plane. At least two additional lenses are tilted with respect to their optical axes relative to the illumination beam path and imaging beam path. The optical axes of the two additional lenses and the optical axis of the illumination beam path and imaging beam path lie in a second plane which intersects the first plane substantially along the optical axis of the illumination beam path and imaging beam path.

The tilting of the lenses in two planes extending perpendicular to one another brings about matching of the imaging scales for two sections extending perpendicular to one another. The images are less distorted and similarity of imaging is achieved. Further, the axial astigmatism can be corrected in this way and the rotational symmetry of the errors in the field can be reproduced approximately.

A preferred further development of the invention comprises four collecting lenses which are divided into two lens pairs. The lenses of the first lens pair are tilted in a first plane. The lenses of the second lens pair are tilted in a second plane, these two planes extending perpendicular to one another. It is particularly advantageous when the tilting angle and displacements of the lenses are selected in such a way that the area in the vicinity of the optical axes of the lenses is not penetrated by the illuminating bundle.

This system enables very good matching of the imaging scales for two sections extending perpendicular to one another.

The invention will be described more fully in the following with reference to the drawings.

BRIEF DESCRIPTION OF THE DRAWINGS

In the drawings:

FIG. 1 shows a side view of the optical system according to the invention;

FIG. 2 shows a top view of the optical system according to the invention; and

DESCRIPTION OF THE PREFERRED EMBODIMENTS

Figure 3:
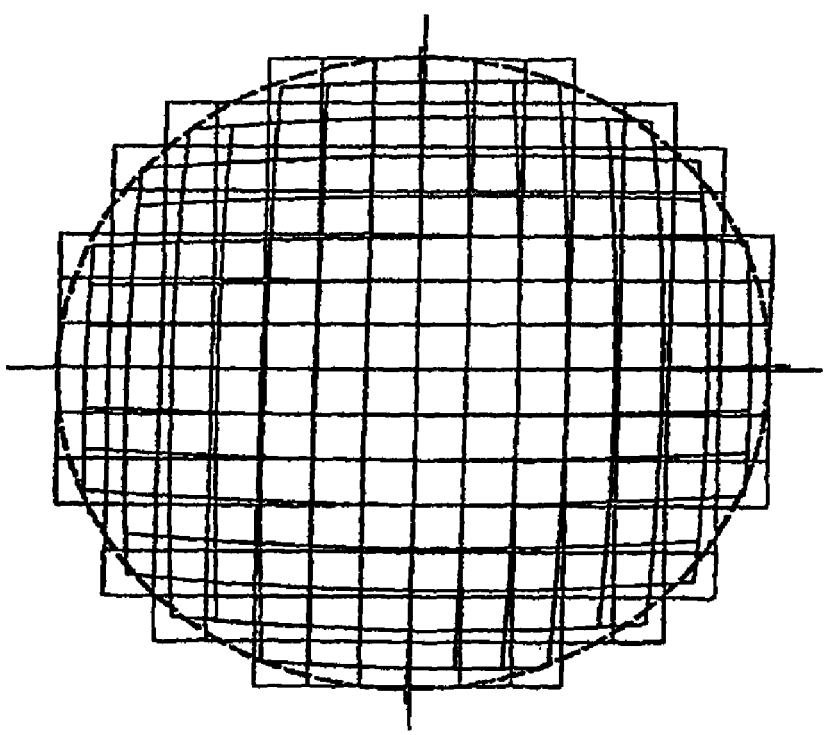
FIG. 3 is a schematic view of the residual distortion.

FIG. 1 is a schematic side view showing the optical system according to the invention, wherein parts that are not substantial to the invention, such as the patient's eye, light sources, photographic device and observation system, are not shown for the sake of simplicity.

Four lenses 1, 2, 3, 4 are so arranged along the optical axis 5 that defines the illumination beam path and imaging beam path of the fundus camera that the lenses 1 and 2 are tilted relative to the drawing plane 6 of FIG. 1, while lenses 3 and 4 are tilted relative to the optical axis 5 within the drawing plane 6 so that their optical axes 7 and 8 likewise lie in the drawing plane 6.

FIG. 2 shows a top view of the optical system. The drawing plane 9 is accordingly perpendicular to the drawing plane 6 of FIG. 1. The lenses 1 and 2 are tilted within the drawing plane 9 such that their optical axes 10 and 11 lie in the drawing plane 9. The lenses 3 and 4 are accordingly tilted relative to the drawing plane 9.

The lenses are arranged in such a way that the illumination bundle of the imaging beam path and illumination beam path with the optical axis 5 penetrates none of the lenses 1, 2, 3, 4 in their central area, that is, the optical axes 10, 11, 7, 8 of the lenses 1, 2, 3, 4 lie outside the bundle beams shown schematically in FIGS. 1 and 2.

The optical data of a preferred realization of the invention are listed in the following table. Designations with the suffix v pertain to the front sides of the lenses 1, 2, 3, 4 and designations with suffix h pertain to the back sides of the lenses 1, 2, 3, 4.

| No. | Radius of curvature [mm] | Distance to the next surface [mm] | Medium following the surface |
|---|---|---|---|
| Obj. | infinity | 39.42477 | air |
| 1v | −76.12524 | 16.63675 | LaK8 |
| 1h | −50.66730 | −2.16757 | air |
| 2v | −197.58358 | 29.93724 | LaK8 |
| 2h | −89.73436 | 7.92140 | air |
| 3v | 580.99844 | 26.79594 | LaK8 |
| 3h | −260.25600 | −9.88489 | air |
| 4v | 169.89283 | 20.11881 | LaK8 |
| 4h | −1636.24830 | 32.91953 | air |
|  | infinity | 145.13560 | air |

The following table contains the values for the displacements and tilting of the lenses 1, 2, 3, 4 relative to the optical axis 5 that are necessary for realizing this embodiment example.

The distortions resulting with this system are shown in FIG. 3. It can be seen that the imaging scales extensively correspond in the x-direction and y-direction. The comparison grid (straight lines) has the same extension in the x-direction and y-direction. Therefore, the requirements for similarity of imaging are ensured to a very great extent.

Further, the optical system according to the invention is characterized in that the errors at the edge of field are distinctly symmetric with respect to rotation. This makes it possible to compensate for these errors through a rotationally symmetric sequential system.

The following table juxtaposes the essential data of an optical system according to the prior art (U.S. Pat. No. 4,730,910=system A) and according to the invention (system B).

|  | System A | System B |
|---|---|---|
| Pupil Imaging |  |  |
| Length of system [mm] | 60 | 104 |
| Focal length f' [mm] | 31.5 | 57.3 |
| Pupil imaging scale $\beta_{px}$ | −2.19 | −2.5 |
| $\beta_{py}$ | −2.46 | −2.5 |
| Imaging length $l'_p$ [mm] | 171.6 | 304 |
| Working distance [mm] | 24.2 | 38.1 |
| Field angle illumination [°] | 23.5 | 26 |
| Average spot radius (axis) [mm] | 0.9974 | 0.2349 |
| Average spot radius (field) [mm] | 1.2532 | 0.4334 |
| Petzval curvature $r_p$ [mm] | −71.9424 | −93.4579 |
| Distortion | 2.64% | 0.74% |
| Longitudinal color aberration $S_e$-$S_C$ [mm] | −3.13 | −5.76 |
| Longitudinal color aberration $S_e$-$S_F$ [mm] | 3.08 | 5.66 |
| Object imaging |  |  |
| Field angle observation [°] | 22.5 | 25 |
| Average spot radius (axis) [mm] | 0.0119 | 0.0020 |
| Average spot radius (field) [mm] | 0.0575 | 0.0158 |
| Distortion | −13.01% | −9.43% |
| Longitudinal color aberration $S_e$-$S_C$ [µm] | −17 | −7.6 |
| Longitudinal color aberration $S_e$-$S_F$ [µm] | 18 | 8.9 |

|  |  | Displacement [mm] | | Rotation [°] | | Placement of center of rotation |
|---|---|---|---|---|---|---|
| Surface No. | Type of decentering | x-direction | y-direction | around x-axis | around y-axis | in z-direction [mm] |
| 1v | 1. Displacement, 2. rotation | 10.1400 | 1.0882 | 0.000 | 29.760 | −23.8578 |
| 1h | 1. Displacement, 2. rotation | 10.1400 | 1.0882 | 0.000 | 29.760 | −40.4946 |
| 2v | 1. Displacement, 2. rotation | −6.5758 | 1.0882 | 0.000 | −18.959 | −93.6604 |
| 2h | 1. Displacement, 2. rotation | −6.5758 | 1.0882 | 0.000 | −18.959 | −123.5976 |
| 3v | 1. Displacement, 2. rotation | 15.5328 | −34.7519 | 5.988 | 0.000 | −202.8670 |
| 3h | 1. Displacement, 2. rotation | 15.5328 | −34.7519 | 5.988 | 0.000 | −229.6629 |
| 4v | 1. Displacement, 2. rotation | 15.5328 | −82.9383 | 14.841 | 0.000 | 465.0016 |
| 4h | 1. Displacement, 2. rotation | 15.5328 | −82.9383 | 14.841 | 0.000 | 444.8823 |
|  | 1. Displacement, 2. rotation, rotated coordinates also apply for the subsequent surfaces | 3.7576 | −5.0827 | 2.447 | 4.089 | 0.0000 |

A significant improvement over the prior art is achieved in all of the relevant parameters for imaging quality.

In the realization according to the invention, it is possible to replace the lenses shown in FIGS. 1 and 2 with corresponding lens segments which encompass at least the area of the penetration of the illumination beam path and the imaging beam path.

The invention is not limited to the embodiment example shown herein. In certain cases, it may also be advantageous when the two tilting planes are not perpendicular to one another.

In order to improve the optical imaging characteristics, it can be advantageous to provide at least one of the lenses with an aspheric surface. It is also possible to realize the invention by using diffractive optical elements instead of one or more lenses.

The principle of the invention is also applicable in other fields in which flare must be suppressed at optical surfaces.

While the foregoing description and drawings represent the present invention, it will be obvious to those skilled in the art that various changes may be made therein without departing from the true spirit and scope of the present invention.

The invention claimed is:

1. An optical system for observing or photographing a fundus of an eye with a substantially coaxial illumination beam path and imaging beam path, the optical system comprising:
    a lens system of at least four lenses;
    wherein at least two lenses of the at least four lenses are tilted with respect to their optical axes relative to the illumination beam path and imaging beam path;
    wherein the optical axes of the two lenses and optical axis of the illumination beam path and imaging beam path lie in a first plane;
    wherein at least two other lenses of the at least four lenses are tilted with respect to their optical axes relative to the illumination beam path and imaging beam path;
    wherein the optical axes of the two other lenses and optical axis of the illumination beam path and imaging beam path lie in a second plane which intersects the first plane substantially along the optical axis of the illumination beam path and imaging beam path; and
    wherein the optical axis of the illumination beam path and imaging beam path penetrates the lens outside their optical axes.

2. The optical system according claim 1;
    wherein the first plane and the second plane extend substantially perpendicular to one another.

3. The optical system according to claim 1;
    wherein the optical axes of the lenses are arranged outside the beam bundle of the illumination beam path and imaging beam path.

4. The optical system according to claim 1;
    wherein the lenses comprise lens segments.

5. The optical system according to claim 1;
    wherein at least one of the lenses has an aspheric surface.

6. The optical system according to claim 1;
    wherein at least one lens is replaced by a diffractive optical element.

* * * * *